(12) United States Patent
Reed et al.

(10) Patent No.: US 11,666,439 B2
(45) Date of Patent: Jun. 6, 2023

(54) INVERTED HEART VALVE FOR TRANSCATHETER VALVE REPLACEMENT

(71) Applicant: Anteris Technologies Corporation, Eagan, MN (US)

(72) Inventors: Andrew Reed, Eagan, MN (US); Dave Mathieu, Eagan, MN (US); Philip J. Haarstad, Eagan, MN (US); Alex A. Peterson, Eagan, MN (US); William Morris Leonard Neethling, Eagan, MN (US); Tuan Doan, Eagan, MN (US); Christopher P. Olig, Eagan, MN (US); Scott Bliss, Eagan, MN (US)

(73) Assignee: Anteris Technologies Corporation, Eagan, MN (US)

( * ) Notice: Subject to any disclaimer, the term of this patent is extended or adjusted under 35 U.S.C. 154(b) by 371 days.

(21) Appl. No.: 17/056,004

(22) PCT Filed: May 20, 2019

(86) PCT No.: PCT/US2019/033165
§ 371 (c)(1),
(2) Date: Nov. 17, 2020

(87) PCT Pub. No.: WO2019/222755
PCT Pub. Date: Nov. 21, 2019

(65) Prior Publication Data
US 2021/0212822 A1 Jul. 15, 2021

Related U.S. Application Data

(60) Provisional application No. 62/673,217, filed on May 18, 2018, provisional application No. 62/674,858, filed on May 22, 2018.

(51) Int. Cl.
*A61F 2/24* (2006.01)
*A61F 2/00* (2006.01)
*A61F 2/95* (2013.01)

(52) U.S. Cl.
CPC .......... *A61F 2/2436* (2013.01); *A61F 2/0095* (2013.01); *A61F 2/2418* (2013.01);
(Continued)

(58) Field of Classification Search
CPC .... A61F 2/2436; A61F 2/0095; A61F 2/2418; A61F 2/2439; A61F 2/95;
(Continued)

(56) References Cited

U.S. PATENT DOCUMENTS 4,624,822 A 11/1986 Arru et al.
6,491,511 B1 12/2002 Duran et al.
(Continued)

FOREIGN PATENT DOCUMENTS

CN 203736349 7/2014
EP 2777618 A1 9/2014
(Continued)

OTHER PUBLICATIONS

Knee Hiang Lim et al., Flat or Curved Pericardial Aortic Valve Cusps: A Finite Element Study, Journal of Heart Valve, vol. 13, No. 5 (Sep. 2004).
(Continued)

*Primary Examiner* — Suzette J Gherbi

(57) ABSTRACT

A valve for endovascular heart valve repair that provides improved sealing of the valve against the native wall. The valve assembly has a sealing region at a distal end of the valve. The sealing region having a delivery position and a sealing position, wherein in the delivery position, the sealing region has a first length, and in the sealing position, the sealing region has a second length less than the first length
(Continued)

and a thickness in the sealing position is greater in the sealing position than in the delivery position.

19 Claims, 9 Drawing Sheets

(52) U.S. Cl.
CPC .............. *A61F 2/2439* (2013.01); *A61F 2/95* (2013.01); *A61F 2002/9534* (2013.01); *A61F 2250/0069* (2013.01)

(58) Field of Classification Search
CPC ...... A61F 2002/9534; A61F 2250/0069; A61F 2220/0025
See application file for complete search history.

(56) References Cited

U.S. PATENT DOCUMENTS

| | | | |
|---|---|---|---|
| 6,682,559 | B2 | 1/2004 | Myers et al. |
| 7,025,780 | B2 | 4/2006 | Gabbay |
| 7,087,079 | B2 | 8/2006 | Navia et al. |
| 8,778,018 | B2 | 7/2014 | Iobbi |
| 8,992,599 | B2 | 3/2015 | Thubrikar et al. |
| 9,011,525 | B2 | 4/2015 | Claiborne, III et al. |
| 9,095,430 | B2 | 8/2015 | Cunanan et al. |
| 9,192,470 | B2 | 11/2015 | Cai et al. |
| 9,205,172 | B2 | 12/2015 | Neethling et al. |
| 9,259,313 | B2 | 2/2016 | Wheatley |
| 9,301,835 | B2 | 4/2016 | Campbell et al. |
| 9,554,902 | B2 | 1/2017 | Braido et al. |
| 9,744,037 | B2 | 8/2017 | Kheradvar et al. |
| 9,763,780 | B2 | 9/2017 | Morriss et al. |
| 11,135,059 | B2 | 10/2021 | Hammer et al. |
| 11,464,635 | B2 | 10/2022 | Reimer et al. |
| 2003/0069635 | A1 | 4/2003 | Cartledge et al. |
| 2005/0123582 | A1 | 6/2005 | Sung et al. |
| 2005/0137687 | A1 | 6/2005 | Salahieh et al. |
| 2005/0203614 | A1* | 9/2005 | Forster ................. A61F 2/2418 623/2.11 |
| 2005/0240262 | A1 | 10/2005 | White |
| 2006/0020327 | A1 | 1/2006 | Lashinski et al. |
| 2008/0288055 | A1 | 11/2008 | Paul, Jr. |
| 2010/0049313 | A1 | 2/2010 | Alon et al. |
| 2011/0066224 | A1 | 3/2011 | White |
| 2011/0238167 | A1 | 9/2011 | Dove et al. |
| 2012/0277855 | A1 | 11/2012 | Lashinski et al. |
| 2013/0018458 | A1 | 1/2013 | Yohanan et al. |
| 2013/0184811 | A1 | 7/2013 | Rowe et al. |
| 2013/0204360 | A1 | 8/2013 | Gainor |
| 2013/0310927 | A1 | 11/2013 | Quintessenza |
| 2014/0005772 | A1 | 1/2014 | Edelman et al. |
| 2014/0031924 | A1 | 1/2014 | Bruchman et al. |
| 2014/0277417 | A1 | 9/2014 | Schraut et al. |
| 2014/0324160 | A1 | 10/2014 | Benichou et al. |
| 2015/0134056 | A1 | 5/2015 | Claiborne, III et al. |
| 2015/0142104 | A1 | 5/2015 | Braido |
| 2015/0209141 | A1 | 7/2015 | Braido et al. |
| 2015/0216663 | A1 | 8/2015 | Braido et al. |
| 2015/0320556 | A1 | 11/2015 | Levi et al. |
| 2016/0128831 | A1 | 5/2016 | Zhou et al. |
| 2016/0135951 | A1 | 5/2016 | Salahieh et al. |
| 2016/0143732 | A1 | 5/2016 | Glimsdale |
| 2016/0158007 | A1 | 6/2016 | Centola et al. |
| 2016/0175095 | A1 | 6/2016 | Dienno et al. |
| 2016/0220365 | A1 | 8/2016 | Backus et al. |
| 2016/0317293 | A1 | 11/2016 | Matheny et al. |
| 2016/0331532 | A1 | 11/2016 | Quadri |
| 2016/0367360 | A1 | 12/2016 | Cartledge et al. |
| 2016/0367364 | A1 | 12/2016 | Torrianni et al. |
| 2017/0049566 | A1 | 2/2017 | Zeng et al. |
| 2017/0056170 | A1 | 3/2017 | Zhu et al. |
| 2017/0119525 | A1 | 5/2017 | Rowe et al. |
| 2017/0189174 | A1 | 7/2017 | Braido et al. |
| 2017/0312075 | A1 | 11/2017 | Fahim et al. |
| 2018/0028312 | A1 | 2/2018 | Thill et al. |
| 2018/0228603 | A1 | 8/2018 | Racchini et al. |
| 2019/0117390 | A1 | 4/2019 | Neethling et al. |
| 2021/0212819 | A1 | 7/2021 | Reed et al. |
| 2021/0212822 | A1 | 7/2021 | Reed et al. |
| 2021/0212823 | A1 | 7/2021 | Reed et al. |

FOREIGN PATENT DOCUMENTS

| | | |
|---|---|---|
| EP | 3697343 | 8/2020 |
| JP | 2008-264553 | 11/2008 |
| JP | 2015519187 A | 7/2015 |
| WO | 2001076510 A2 | 10/2001 |
| WO | 2003/030776 | 4/2003 |
| WO | 2007013999 A2 | 2/2007 |
| WO | 2011072084 A2 | 6/2011 |
| WO | 2011109450 A2 | 9/2011 |
| WO | 2014204807 A1 | 12/2014 |
| WO | 2015126712 A1 | 8/2015 |
| WO | 2015173794 A1 | 11/2015 |
| WO | 2017031155 A1 | 2/2017 |

OTHER PUBLICATIONS

Search Report and Written Opinion for related PCT Application No. PCT/US2019/033165 dated Sep. 3, 2019 (10 pages).

* cited by examiner

INVERTED HEART VALVE FOR TRANSCATHETER VALVE REPLACEMENT

CROSS-REFERENCE TO RELATED APPLICATIONS

The present disclosure claims priority to U.S. Provisional Application No. 62/673,217, and filed May 18, 2018, and U.S. Provisional Application No. 62/674,858, filed May 22, 2018, entitled "Inverted Heart Valve For Transcatheter Valve Replacement", the contents of which are hereby incorporated by reference herein in their entirety.

FIELD OF THE INVENTION

The present disclosure relates to novel and advantageous devices and methods for a transcatheter valve replacement devices.

BACKGROUND OF THE INVENTION

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Native heart valves may need to be replaced when a patient has a condition such as congenital heart defect or valvular heart disease. A diseased heart valve may result in regurgitation, where the valve is not properly function and blood flows in a direction opposite the normal direction of the flow, and/or stenosis, where the valve has narrowed through in some instances calcification of the valve, some obstruction of the valve such as plaque, or inflammation. Heart valves may be replaced through surgical repair or a valve deployed relative to the native heart valve through a transcatheter approach. Transcatheter valve replacement devices generally comprise leaflets of tissue that are attached to an expandable or self-expanding stent construct that is crimped onto a catheter for deployment. The stent is advanced to the location of the troubled heart valve, where it expands or is expanded by a balloon or other means. Once seated in the valve, blood flow and the muscles of the heart will result in the tissue leaflets to open and close.

One challenge affecting transcatheter valve replacement devices is the French size of the catheter required to deliver the valve replacement device to the affected native heart valve through the vasculature. There is a desire to reduce the French size of the catheter to improve maneuverability of the catheter as it is advanced to the site of the affected native heart valve.

BRIEF SUMMARY OF THE INVENTION

The following presents a simplified summary of one or more embodiments of the present disclosure in order to provide a basic understanding of such embodiments. This summary is not an extensive overview of all contemplated embodiments, and is intended to neither identify key or critical elements of all embodiments, nor delineate the scope of any or all embodiments.

A heart valve of the present disclosure is loaded onto a delivery catheter in an inverted position relative to a stent of a heart valve assembly. The heart valve is attached at a proximal end of the heart valve to a distal end of the stent in the loaded position. The heart valve assembly has at least one or more gripper fingers releasably attached to the stent at a proximal end of the stent at a proximal end of the stent. The gripper fingers are connected to the handle of the catheter at a proximal end of the catheter. At least one or more cable lines are attached to a portion of the heart valve and extend proximally through the sheath to the handle of the catheter. The valve is pulled proximally through the lumen of the stent to a working position.

In some embodiments of the present disclosure, a system for endovascular heart valve repair comprises a delivery catheter and a valve assembly. The deliver catheter may comprise a retractable sheath and a tip near a distal end of the catheter. The valve assembly may be disposed within the retractable sheath in a delivery position. The valve assembly may comprise an expandable stent with a valve in an inverted orientation. The expandable stent has a proximal end, a distal end, an outer surface, and an inner surface that defines a stent lumen. The valve has a proximal end that may be connected to the distal end of the expandable stent. The valve has an outer surface and an inner surface defining a valve lumen. The valve may extend distally from the distal end of the expandable stent between the expandable stent and the tip when the valve assembly is in the delivery position. In some embodiments, the system may further comprise at least one cable wire removably connected to the valve at least substantially near the distal end of the valve. After the expandable stent has been at least partially expanded, the at least one cable wire may be pulled in a proximal direction to pull the distal end of the valve through the valve lumen and through at least a portion of the stent lumen to transpose the valve from the inverted orientation in the delivery position to a deployed position.

In some embodiments, the system may further comprise at least one locking feature on the expandable stent. In some embodiments, the at least one locking feature is substantially near the distal end of the expandable stent. When the valve is in the deployed position, the at least one locking feature on the stent may be engaged with the valve. In some embodiments, the at least one locking feature on the stent may be engaged with the distal end of the valve. In some embodiments, when the locking feature on the stent is engaged with the valve, the at least one cable wire is disconnected from the valve.

In some embodiments, the system may further comprise at least one gripping finger removably engaged with the proximal end of the expandable stent. The at least one gripping finger may be disposed between the retractable sheath and an inner shaft of the delivery catheter. After the expandable stent has been at least partially expanded, a retrieving force may be applied to the at least one gripping finger in a proximal direction to pull the valve assembly into the retractable sheath for repositioning of the valve assembly.

A method of endovascularly delivering a heart valve assembly may comprise retracting a retractable sheath of a delivery catheter, wherein a valve assembly is disposed within the retractable sheath, the valve assembly comprising an expandable stent and an inverted valve having a proximal end connected to a distal end of the expandable stent, wherein the inverted valve extends distally from the expandable stent towards a distal end of the delivery catheter; expanding the valve assembly from the delivery position into an expanded position; and pulling a distal end of the inverted valve through the valve lumen and at least a portion of the stent lumen to a deployed position using at least one cable wire connected to the inverted valve. The method may further comprise locking the distal end of the inverted valve to the stent. The method may further comprise releasing the at least one cable wire from the inverted valve. The method may further comprise recapturing the valve assembly through the retractable sheath to reposition the valve assembly.

In some embodiments of the present disclosure, a valve assembly for endovascular heart valve repair, the valve assembly may comprise an expandable stent having a proximal end and a distal end, the expandable stent having an outer surface and an inner surface defining a stent lumen; and a valve having a proximal end and a distal end, the proximal end of the valve connected to the distal end of the expandable stent, the valve having an outer surface and an inner surface defining a valve lumen. The valve may be in an inverted orientation in a delivery position of the valve assembly and then transposed into a working position when the valve assembly is in a deployed position.

While multiple embodiments are disclosed, still other embodiments of the present disclosure will become apparent to those skilled in the art from the following detailed description, which shows and describes illustrative embodiments of the invention. As will be realized, the various embodiments of the present disclosure are capable of modifications in various obvious aspects, all without departing from the spirit and scope of the present disclosure. Accordingly, the drawings and detailed description are to be regarded as illustrative in nature and not restrictive.

BRIEF DESCRIPTION OF THE DRAWINGS

While the specification concludes with claims particularly pointing out and distinctly claiming the subject matter that is regarded as forming the various embodiments of the present disclosure, it is believed that the invention will be better understood from the following description taken in conjunction with the accompanying Figures, in which:

DETAILED DESCRIPTION

The present disclosure relates to replacement heart valves for use in the mitral valve, tricuspid valve, aortic valve or pulmonary valve of the heart. In some circumstances, a replacement heart valve may be disposed within the native valve such that portions of the replacement heart valve, or portions of a device such as a stent attached to the replacement heart valve, are adjacent to the native heart valve.

In the following detailed description, numerous specific details are set forth in order to provide a thorough understanding of some embodiments. However, it will be understood by persons of ordinary skill in the art that some embodiments may be practiced without these specific details. In other instances, well-known methods, procedures, components, units and/or circuits have not been described in detail so as not to obscure the discussion. Although this application uses the terms "proximal" and "distal" in the same relative manner with respect to the devices shown in the figures, it is within the scope of this invention that "proximal" and "distal" can be interchanged with "distal" and "proximal" in other embodiments.

In prior valve replacement devices, the valve assembly is loaded within a catheter assembly with the valve wrapped inside the stent's lumen, and, in some instances, the valve is even wrapped about a balloon within the stent's lumen for balloon-expandable stents. This creates a significant thickness of the valve assembly in the delivery position. Thus, a larger French size of the catheter assembly needed to deliver deploy the valve. Larger French sizes and thicker sections reduce flexibility and eliminate potential entry points in the vasculature due to size of the catheter necessary to deliver and deploy the valve. The embodiments of this invention reduce the thickness of the valve assembly in the delivery position to enable a reduction in the French size of the catheter needed for delivery of the valve assembly to a valve repair site.

Figure 1:
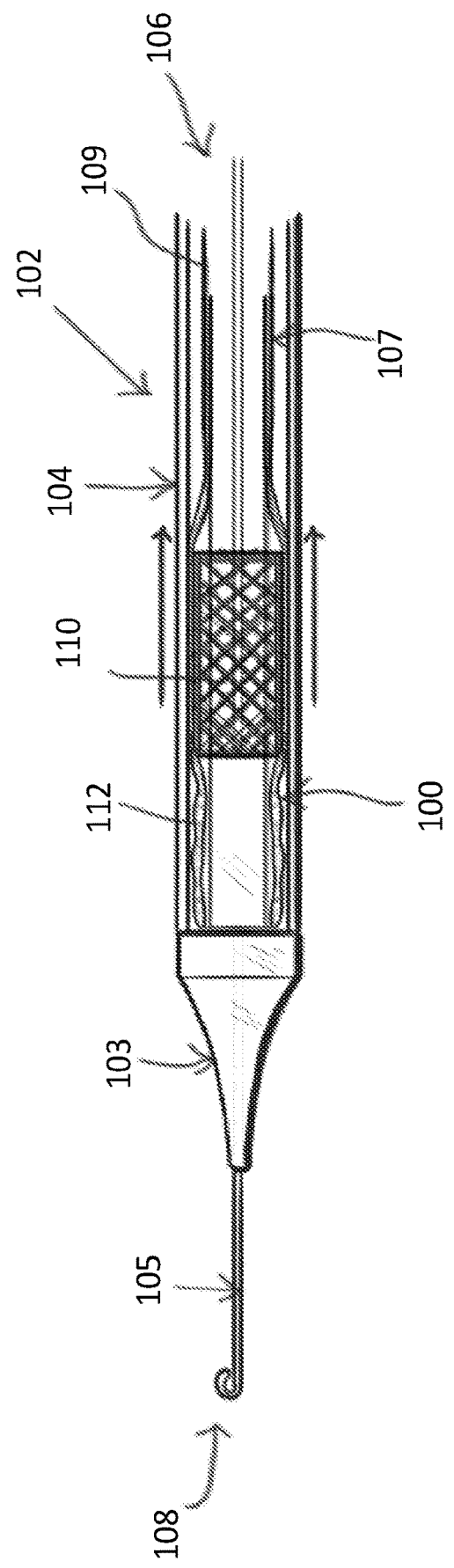
FIG. 1 is a side view of a replacement heart valve assembly disposed within the retractable sheath of a catheter in a delivery position.

FIGS. 1-9 show an embodiment of the present disclosure. FIG. 1 shows a valve assembly 100 of the present disclosure loaded within a catheter assembly 102 in a delivery position. The valve assembly 100 comprises a stent 110 and a valve 112 in an inverted position, where the valve 112 is disposed generally distally of the stent 110. By having the valve 112 disposed generally distally of the stent in the delivery position, this reduces the size of the catheter needed for delivery of the valve assembly to a valve repair site.

The catheter assembly 102 has a retractable sheath 104 with a proximal end 106 and a distal end 108. The catheter assembly 102 may further comprise a tip 103 near the distal end 108, a guidewire 105, and an inner shaft 107 coaxial with the retractable sheath 104. The guidewire 105 may be disposed within the inner shaft 107. The catheter assembly 102 may comprise at least one inversion wire 109 connected to the valve assembly 100 for pulling at least a portion of the valve assembly 100 in an axial direction through the stent to transpose the valve 112 from its inverted, delivery position into a deployed position. The at least one inversion wire 109 may be positioned between the inner shaft 107 and the retractable sheath 104. As shown in FIG. 1, the catheter assembly 102 has at least two inversion wires 109, although it is contemplated by this disclosure that any number of inversion wires 109 may be suitable to control the inversion of the valve 112. The catheter assembly 102 may further comprise at least two guide fingers 111 connected to the valve assembly 100 for positioning of the valve assembly 100, and also allow for repositioning the valve assembly 100 once the valve assembly is at least partially deployed.

The stent 110 may be a balloon expandable, self-expanding, or otherwise expandable stent capable of expanding from a delivery position to a deployed position. The stent 110 has a distal end 114, a proximal end 116, an outer surface 118 extending between the distal end 114 and the proximal end 116, and an inner surface 120 extending between the distal end 114 and the proximal end 116 and defining a stent lumen 122 therein. In the delivery position, the guide fingers 111 are engaged with the proximal end 116 of the stent 110. The stent 110 comprises a plurality of struts 117. In some embodiments the distal end 114 of the stent has a crown-like strut pattern for attachment to the valve 112. The valve 112 may be sutured or otherwise adhered to a distal end 114 of the stent.

The valve 112 may comprise a tissue material. The valve 112 may be constructed, in some embodiments, from a single piece of tissue material. In some embodiments, the tissue material is an implantable biomaterial such as the biomaterial described in the disclosure of U.S. Patent Provisional App. Ser. No. 62/574,410 filed on Oct. 19, 2017 and entitled "Replacement Heart Valve with Reduced Suturing," which is incorporated by reference herein in its entirety. In other embodiments, the valve 112 may be constructed from multiple pieces of tissue material. In some embodiments, the tissue material may be a biomaterial. In some embodiments, the tissue material may be a cross-linked collagen based-biomaterial that comprises acellular or cellular tissue selected from the group consisting of cardiovascular tissue, heart tissue, heart valve, aortic roots, aortic wall, aortic leaflets, pericardial tissue, connective tissue, dura mater, dermal tissue, vascular tissue, cartilage, pericardium, ligament, tendon, blood vessels, umbilical tissue, bone tissue, fasciae, and submucosal tissue and skin. In some embodiments, the tissue material is an implantable biomaterial such as the biomaterial described in the disclosure of U.S. Pat. No. 9,205,172, filed on Dec. 21, 2005 and entitled "Implantable Biomaterial and Method of Producing Same," which is incorporated by reference herein in its entirety. In some embodiments, the tissue material may be artificial tissue. In some embodiments, the artificial tissue may comprise a single piece molded or formed polymer. In some embodiments, the artificial tissue may comprise polytetrafluoroethylene, polyethylene terephthalate, other polymers, and other polymer coatings.

The valve 112 has a distal end 124, a proximal end 126, an outer surface 128 extending between the distal end 124 and the proximal end 126, and an inner surface 130 extending between the distal end 124 and the proximal end 126 and defining a valve lumen 132 therein. The valve 112 is positioned generally distally of the stent 110, and the inner surface 130 overlaps at least a portion of the inner shaft 107. In some embodiments, the valve 112 may be wrapped in a desirable manner around the inner shaft 107 to reduce the profile. In some embodiments, the valve 112 may be directly connected to the stent 110. In other embodiments, the valve 112 may not be directly connected to the stent 110 at least while in the delivery position.

The valve assembly 100 may be delivered to the repair site in the delivery position shown in FIG. 1. Once at the delivery position, the retractable sheath 104 can be pulled in a proximal direction to deploy the valve assembly 100 at the repair site.

Figure 2:
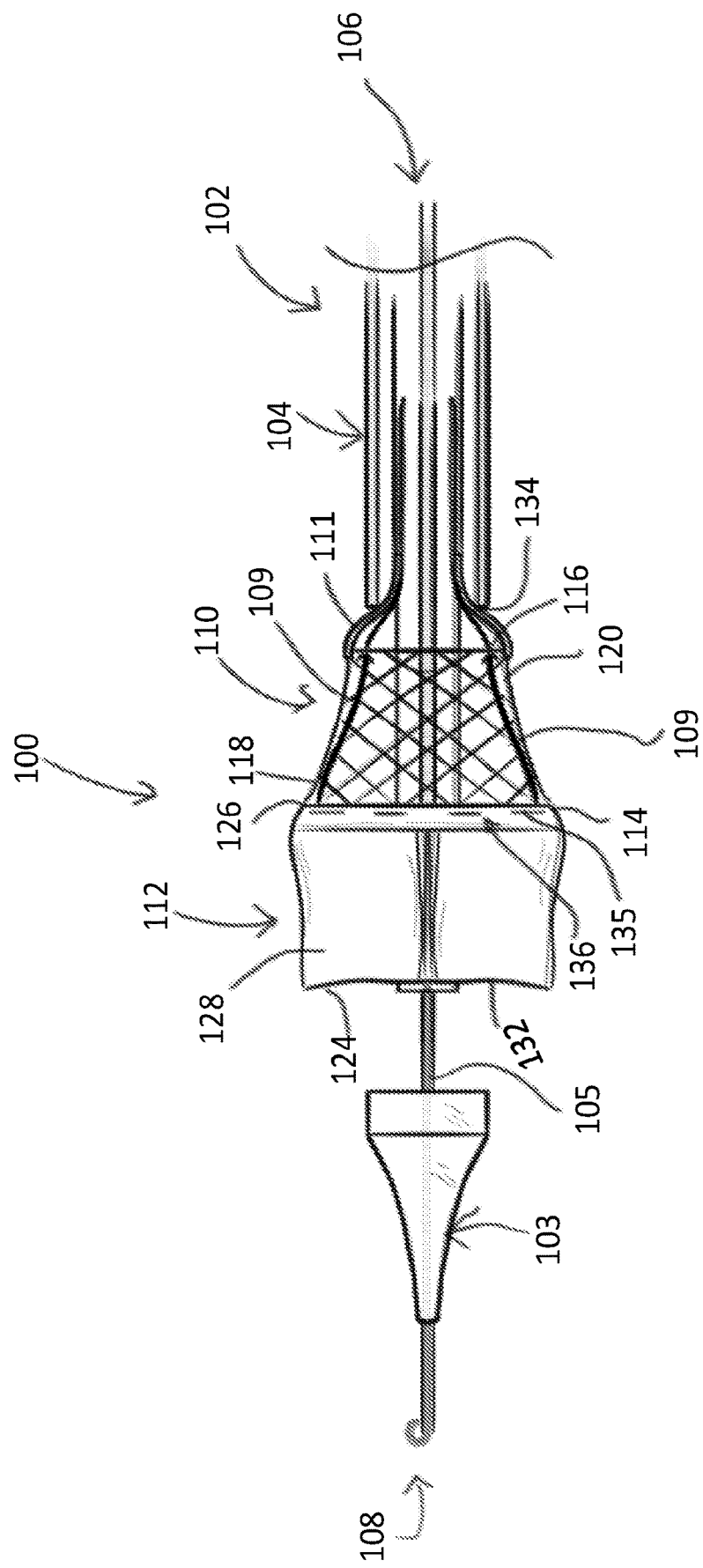
FIG. 2 is a side view of the replacement heart valve assembly of FIG. 1 in a partially expanded position.

FIG. 2 shows the valve assembly 100 in at least a partially expanded position. As shown in FIG. 2, the retractable sheath 104 has been moved to a position that is proximal of the proximal end 116 of the stent 110. In some embodiments, a distal end 134 of the retractable sheath 104 may be in contact with the guide fingers 111 as the valve assembly 100 expands to at least the partially expanded position.

As shown in FIG. 2, the valve 112 is connected to the stent 110 at the distal end 114 of the stent. More particularly, in some embodiments such as the embodiment shown, the proximal end 126 of the valve is connected to the stent 110 at the distal end 114 of the stent. The valve 112 may be connected to the stent 110 by sutures 135, but may also be connected by staples, adhesive, or any other means of connecting the stent 110 to the valve 112. In at least one embodiment, the valve 112 may have a cuff 136, shown in FIG. 2, at the proximal end 126 that overlaps a portion of the outer surface 118 of the stent 110. The cuff 136 may be relatively thin compared to the thickness of other portions of the valve 112 to keep the profile of the valve assembly 100 while in the delivery position low.

Figure 3:
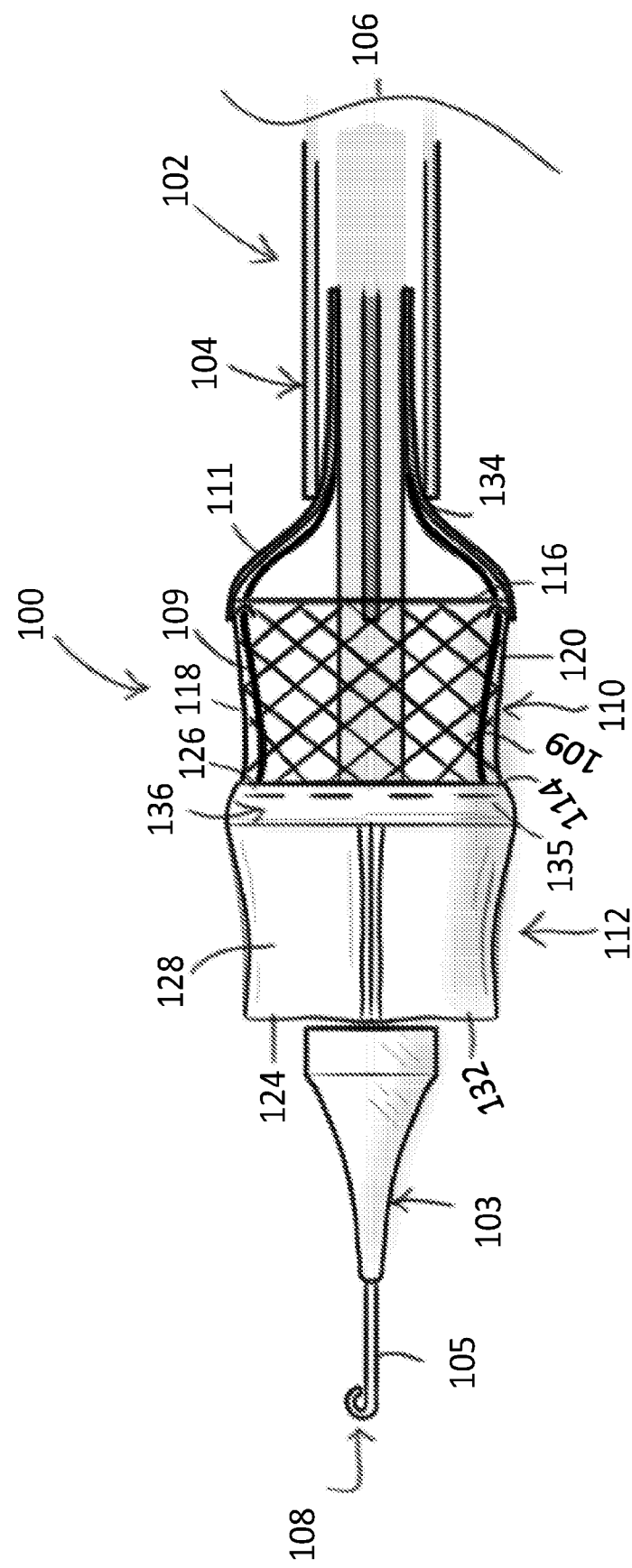
FIG. 3 is a side view of the replacement heart valve assembly of FIG. 1 in fully expanded position with the valve inverted.

FIG. 3 shows the valve assembly 100 with the stent 110 in a fully expanded position. In the fully expanded position, the guide fingers 111 may continue to be engaged with the stent.

Figure 4:
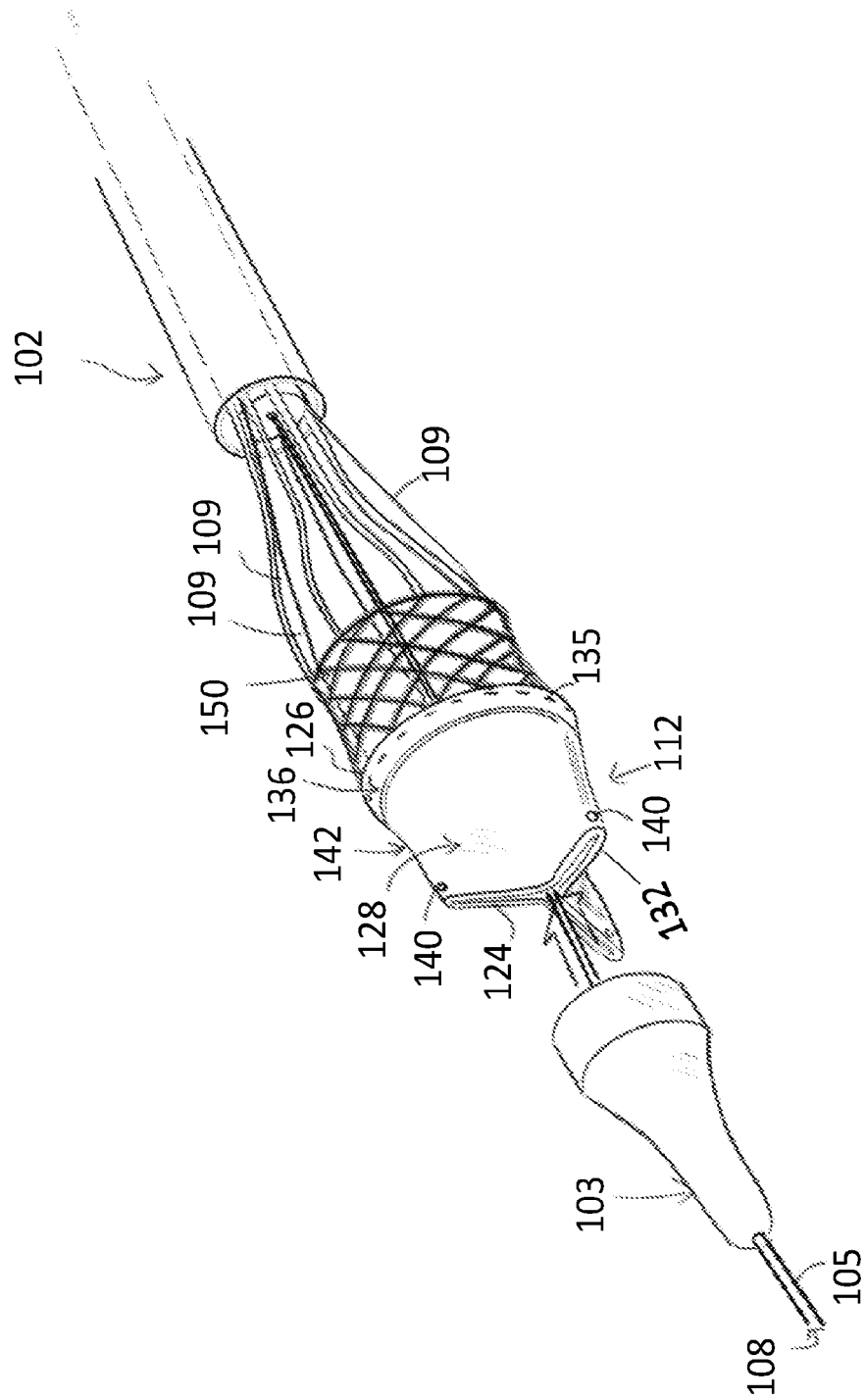
FIG. 4 is a perspective view of the replacement heart valve assembly of FIG. 1 as the valve is being transposed to the partially deployed position.
Figure 5:
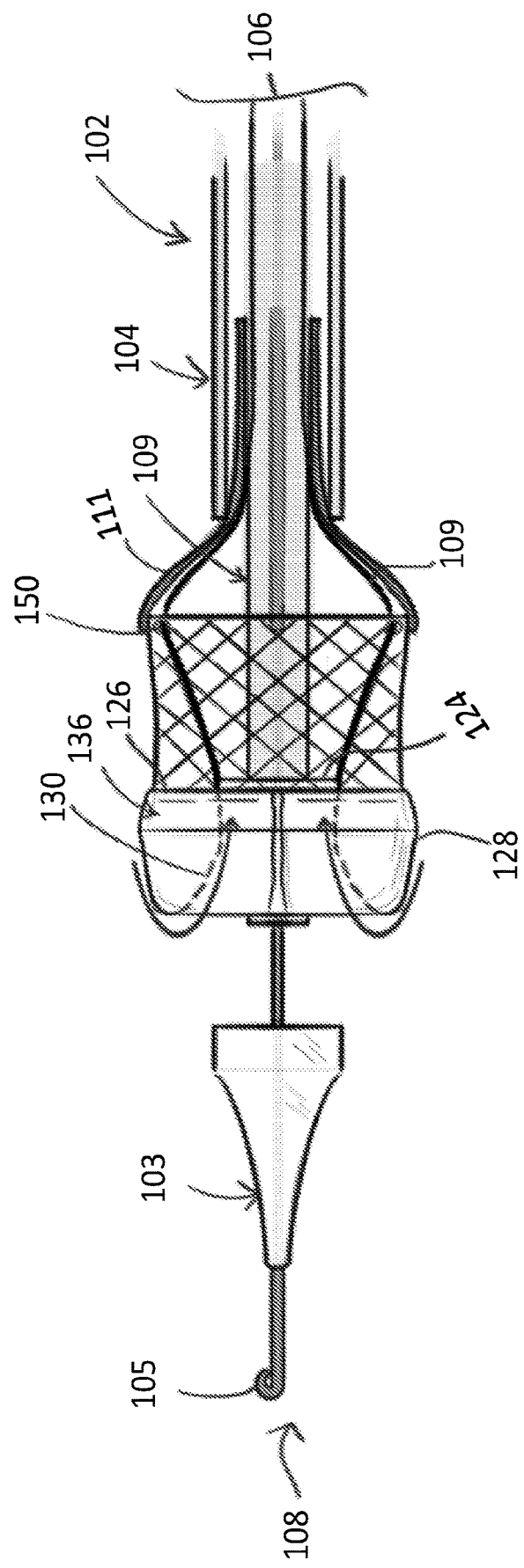
FIG. 5 is a side view of the replacement heart valve assembly of FIG. 1 as the valve is being transposed to the partially deployed position.
Figure 6:
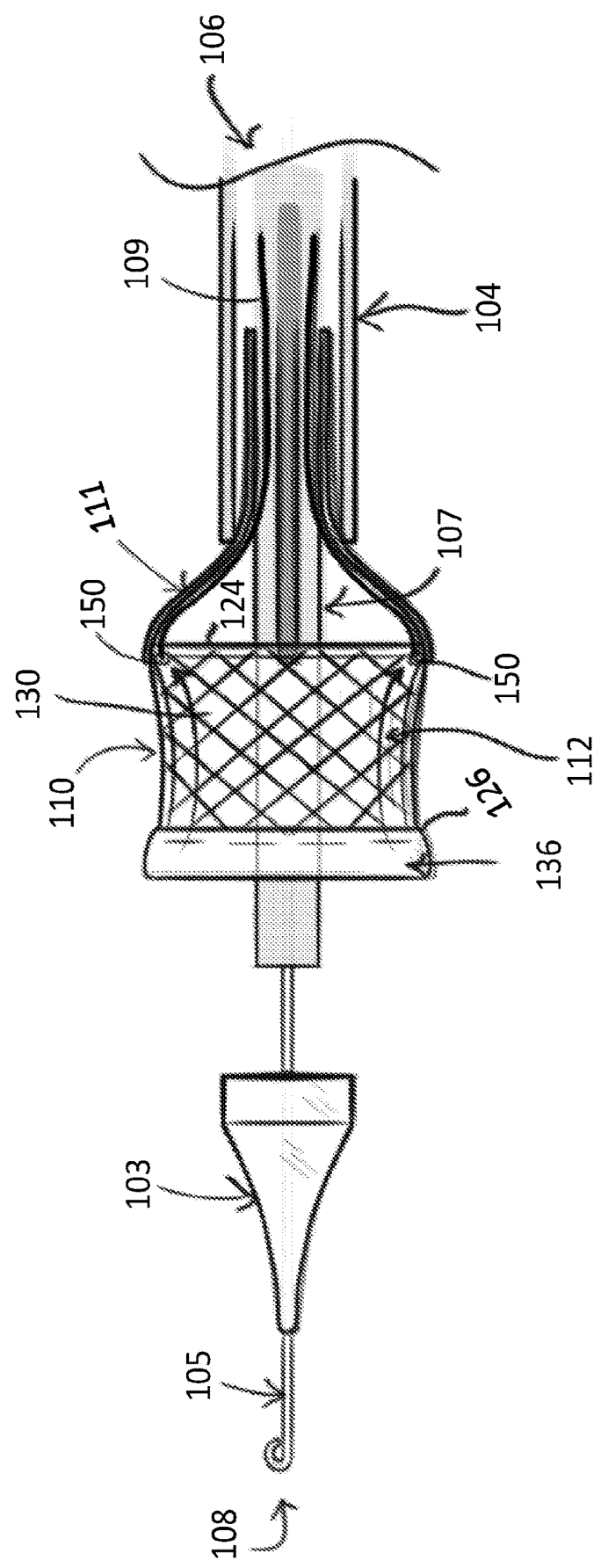
FIG. 6 is a side view of the replacement heart valve assembly of FIG. 1 as the valve in the partially deployed position and locked to the stent.

FIGS. 4-5 show the valve assembly 100 as the valve 112 is transposed from the inverted orientation to a working orientation within the stent lumen of the fully expanded stent 110. As shown best in FIG. 4, the valve 112 may have a number of attachment points 140 at the distal end of the valve 112 for connecting the inversion wires to the valve 112. In at least one embodiment, the valve 112 has three commissures 142 and an attachment point 140 at each commissure. In at least one embodiment, the attachment points 140 may also have locking features for engaging with locking features on the stent. As shown best in FIG. 5, the stent may have inversion openings 150 engaged with the inversion wires 109. In some embodiments the inversion openings 150 may have locking features for engaging with locking features on the valve. As shown in FIGS. 4-5, an axial force is applied in the proximal direction on at least one of the inversion wires 109 to begin pulling the distal end of the valve 112 through the lumen 132 of the valve and into the lumen 122 of the stent. As the valve 112 is being pulled proximally into the lumen 122 of the stent, at one point the distal end of the valve 124 is positioned proximally of the proximal end 126 of the valve, as shown in FIG. 5. In at least one embodiment, the inversion wires 109 are pulled through the inversion openings 150 of the stent. In at least one embodiment, the valve 112 is pulled over the inner shaft 107 of the catheter. While initially oriented in an inverted orientation, the valve 112 is transposed into the working orientation. In some embodiments, the cuff 136 of the valve remains in the same position in the working orientation and the inverted orientation. FIG. 6 shows the valve assembly 100 in a partially deployed position with the valve 112 now positioned in the working orientation, where the valve 112 is mostly disposed within the stent lumen. In the working orientation, the distal end of the valve is at or substantially near the proximal end of the stent. The inner surface of the valve now abuts the inner surface of the stent. The outer surface of the valve now defines a working valve lumen. In some embodiments, to complete engagement of the valve with the stent in the deployed position, the valve may have locking feature at the distal end of the valve that engage with locking features at a proximal end of the stent. In some embodiments, when the valve locking features engage with the stent locking features, the inversion wires are disconnected from the valve and the stent for withdrawal from the repair site along with the remainder of the catheter assembly. In some embodiments, when the valve locking features engage with the stent locking features, this engagement cuts or clips the inversion wire 109 from the attachment point on the valve. In some embodiments, the valve locking features, the inversion wires, and/or the stent locking features may have radiopaque markers or other imaging markers that assist an operator visually with the transposition of the valve and/or the engagement of the valve with the stent. The engagement of the valve locking features with the stent locking features helps to ensure that the valve is properly positioned in the working orientation and engaged with the stent.

Figure 7:
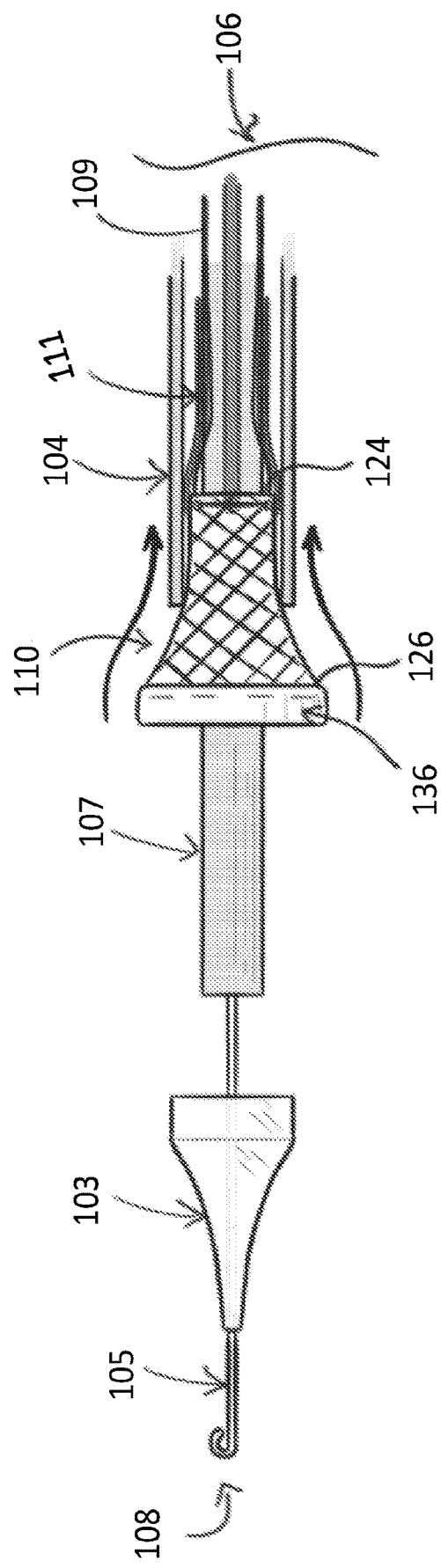
FIG. 7 is a side view of the replacement heart valve assembly of FIG. 1 being recaptured and partially brought back into the sheath for repositioning.
Figure 8:
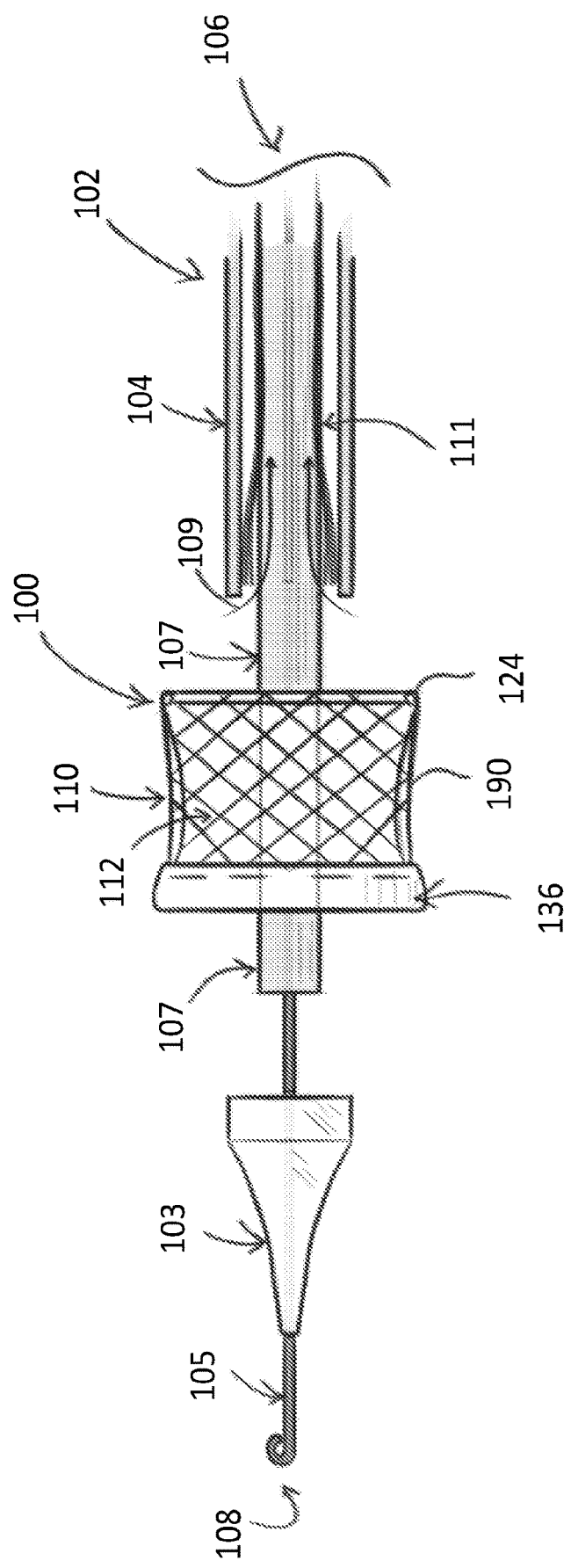
FIG. 8 is a side view of the replacement heart valve assembly of FIG. 1 in the fully deployed position.
Figure 9:
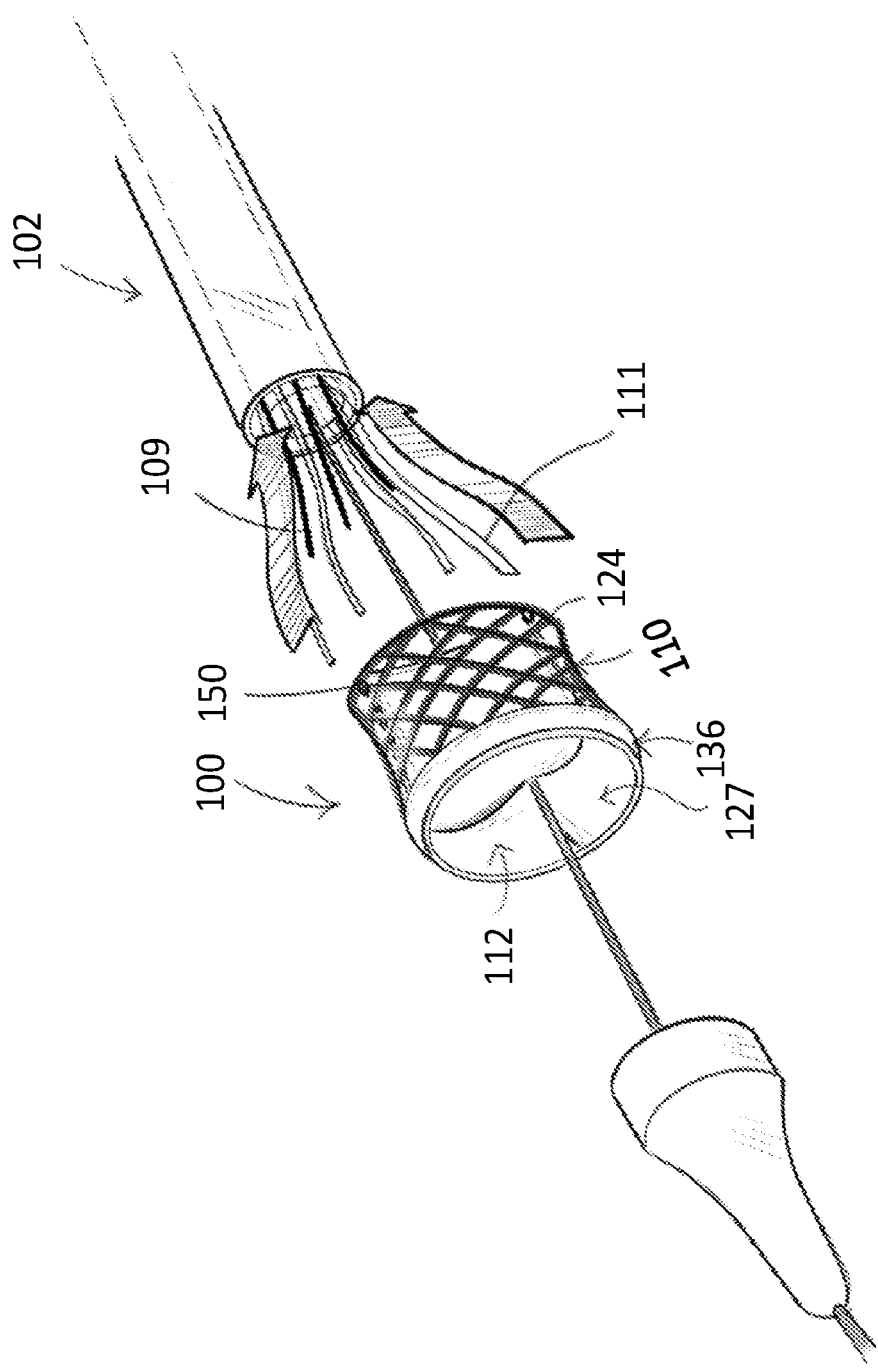
FIG. 9 is a perspective view of the replacement heart valve assembly of FIG. 1 as the valve is being transposed to the partially deployed position.

As can be seen in FIG. 6, the guide fingers 111 continue to grip the proximal end of the valve assembly 100. The guide fingers 111 may be pulled proximally, as shown in FIG. 7, to at least partially resheath the valve within the retractable sheath 104 to reposition the valve, if needed, at the repair site. Once repositioned, the retractable sheath 104 can be withdrawn in the proximal direction again, and the valve assembly can be expanded to its fully expanded and partially deployed position. The guide fingers 111 can then be disengaged from the stent as shown in FIGS. 8-9. In at least one embodiment, the guide fingers 111 may be engaged with guiding features on the stent. The guiding features may be a slot within a strut of the stent at the proximal end of the stent, a channel having a depth less than the thickness of the strut, at least one bump on a surface of the stent, at least one hole, or combinations thereof. The guide fingers 111 may be released from the guiding feature by pushing distally on the gripping fingers to increase the deflection in the guide finger 111 until the guide finger 111 is no longer engaged with the guiding feature.

The catheter assembly is then withdrawn from the vasculature, leaving the fully deployed valve assembly at the repair site. As shown in FIG. 9, when the valve is in the working orientation, the valve leaflets are positioned at the proximal end of the stent. In at least one embodiment, a portion of the inversion wire 190 may remain connected between the valve and the stent to act as a tether. The remaining tether may, in some embodiments, act as a shock absorber for the valve assembly. The pressures involved with the opening and closing of the valve leaflets 127 put significant forces on the commissures of the valve. The tension within the tether, and any resulting deflection within the valve assembly, can assist with dissipation of those forces.

In at least one embodiment, the valve assembly can be packaged in a sterilized packaging system. More specifically, the valve assembly can be packaged with at least a portion of the catheter assembly in the packaging system as described in the disclosure of U.S. Patent Provisional App. Ser. No. 62/533,429 filed on Jul. 17, 2017 and entitled "Sterilized Packaging System For Catheter," which is incorporated by reference herein in its entirety. As described therein, the packaging system may comprise a tray with a plurality of chambers. At least the valve of the valve assembly may be positioned in one chamber of the tray, and the chamber may contain a volume of a sterilizing fluid such as a sterilant. Thus, the valve may be packaged "wet" and may have a first diameter while packaged. In some embodiments, when the valve assembly is removed from the chamber, the valve may shrink (either through mechanical means or the material properties of the valve) and have a second diameter less than the first diameter. The valve assembly may then be pulled proximally through a sheath of the catheter assembly to position the valve assembly within the catheter assembly in the delivery position shown, for example, in FIG. 1. Once the sheath is retracted within the vasculature and the valve is exposed to fluid within the body, the valve may self-expand to the first diameter. In some embodiments, the first diameter may be less than the diameter of the valve when the valve is in the expanded position shown, for example, in FIG. 2.

Although the above disclosure describes a valve assembly comprising both the valve and a stent, it is contemplated by this disclosure that embodiments of this invention may include a valve that is not attached to a stent.

As used herein, the terms "substantially" or "generally" refer to the complete or nearly complete extent or degree of an action, characteristic, property, state, structure, item, or result. For example, an object that is "substantially" or "generally" enclosed would mean that the object is either completely enclosed or nearly completely enclosed. The exact allowable degree of deviation from absolute completeness may in some cases depend on the specific context. However, generally speaking, the nearness of completion will be so as to have generally the same overall result as if absolute and total completion were obtained. The use of "substantially" or "generally" is equally applicable when used in a negative connotation to refer to the complete or near complete lack of an action, characteristic, property, state, structure, item, or result. For example, an element, combination, embodiment, or composition that is "substantially free of" or "generally free of" an ingredient or element may still actually contain such item as long as there is generally no measurable effect thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description should be read to include one or at least one and the singular also includes the plural unless it is obvious that it is meant otherwise.

Still further, the figures depict preferred embodiments for purposes of illustration only. One skilled in the art will readily recognize from the discussion herein that alternative embodiments of the structures and methods illustrated herein may be employed without departing from the principles described herein.

Upon reading this disclosure, those skilled in the art will appreciate still additional alternative structural and functional designs for the devices described herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

While the systems and methods described herein have been described in reference to some exemplary embodiments, these embodiments are not limiting and are not necessarily exclusive of each other, and it is contemplated that particular features of various embodiments may be omitted or combined for use with features of other embodiments while remaining within the scope of the invention. Any feature of any embodiment described herein may be used in any embodiment and with any features of any other embodiment.

What is claimed is:

1. A system for endovascular heart valve repair, the system comprising:
   a delivery catheter comprising a retractable sheath and a tip near a distal end of the catheter; and
   a valve assembly disposed within the retractable sheath in a delivery position, the valve assembly comprising:
   an expandable stent having a proximal end and a distal end, the expandable stent having an outer surface and an inner surface defining a stent lumen; and
   a valve in an inverted orientation having a proximal end and a distal end, the proximal end of the valve connected to the distal end of the expandable stent, the valve having an outer surface and an inner surface defining a valve lumen, wherein the valve extends distally from the distal end of the expandable stent between the expandable stent and the tip when the valve assembly is in the delivery position.

2. The system of claim 1, further comprising:
   at least one cable wire removably connected to the valve at least substantially near the distal end of the valve.

3. The system of claim 2, wherein, after the expandable stent has been at least partially expanded, the at least one cable wire is pulled in a proximal direction to pull the distal end of the valve through the valve lumen and through at least a portion of the stent lumen to transpose the valve from the inverted orientation in the delivery position to a deployed position.

4. The system of claim 3, further comprising:
   at least one locking feature on the expandable stent.

5. The system of claim 4, wherein the at least one locking feature is substantially near the distal end of the expandable stent.

6. The system of claim 4, wherein when the valve is in the deployed position, the at least one locking feature on the stent is engaged with the valve.

7. The system of claim 6, wherein the at least one locking feature on the stent is engaged with the distal end of the valve.

8. The system of claim 6, wherein when the locking feature on the stent is engaged with the valve, the at least one cable wire is disconnected from the valve.

9. The system of claim 1, further comprising:
   at least one gripping finger removably engaged with the proximal end of the expandable stent.

10. The system of claim 9, wherein the at least one gripping finger is disposed between the retractable sheath and an inner shaft of the delivery catheter.

11. The system of claim 9, wherein after the expandable stent has been at least partially expanded, a retrieving force may be applied to the at least one gripping finger in a proximal direction to pull the valve assembly into the retractable sheath for repositioning of the valve assembly.

12. The system of claim 1, further comprising:
   a sterilized packaging system for storing the valve assembly in a stored position prior to loading the valve assembly within the retractable sheath, the sterilized packaging system comprising at least one fluid chamber, wherein in the stored position, the valve is stored wet within the fluid chamber and operably connected to the delivery catheter.

13. A method of endovascularly delivering a heart valve assembly, the method comprising:
   retracting a retractable sheath of a delivery catheter, wherein a valve assembly is disposed within the retractable sheath, the valve assembly comprising an expandable stent and an inverted valve having a proximal end connected to a distal end of the expandable stent, wherein the inverted valve extends distally from the expandable stent towards a distal end of the delivery catheter;
   expanding the valve assembly from the delivery position into an expanded position; and
   pulling a distal end of the inverted valve through the valve lumen and at least a portion of the stent lumen to a deployed position using at least one cable wire connected to the inverted valve.

14. The method of claim 13, further comprising:
   locking the distal end of the inverted valve to the stent.

15. The method of claim 14, further comprising:
   releasing the at least one cable wire from the inverted valve.

16. The method of claim 13, further comprising:
   recapturing the valve assembly through the retractable sheath to reposition the valve assembly.

17. The method of claim 13, further comprising:
   loading the valve into the retractable sheath by pulling the valve proximally within the retractable sheath.

18. The method of claim 13, wherein the valve is stored in a sterilant within a packaging system and the valve assembly is connected to the cable wire while stored within the packaging system.

19. A valve assembly for endovascular heart valve repair, the valve assembly comprising:
   an expandable stent having a proximal end and a distal end, the expandable stent having an outer surface and an inner surface defining a stent lumen; and
   a valve having a proximal end and a distal end, the proximal end of the valve connected to the distal end of the expandable stent, the valve having an outer surface and an inner surface defining a valve lumen,
   wherein the valve is in an inverted orientation in a delivery position of the valve assembly and wherein the valve is disposed within the stent lumen in a deployed position.

* * * * *